(12) United States Patent
Carson et al.

(10) Patent No.: US 8,202,408 B2
(45) Date of Patent: Jun. 19, 2012

(54) SENSOR ELECTRODE AND METHOD FOR THE ELECTROCHEMICAL DETECTION OF NUCLEOTIDES

(75) Inventors: Charles A. Carson, Columbia, MO (US); Hao Li, Columbia, MO (US); Qingsong Yu, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 537 days.

(21) Appl. No.: 12/400,425

(22) Filed: Mar. 9, 2009

(65) Prior Publication Data

US 2009/0283424 A1 Nov. 19, 2009

Related U.S. Application Data

(60) Provisional application No. 61/034,556, filed on Mar. 7, 2008.

(51) Int. Cl.
| | |
|---|---|
| *C12M 1/00* | (2006.01) |
| *C12N 9/00* | (2006.01) |
| *C12N 11/00* | (2006.01) |
| *C25B 9/00* | (2006.01) |
| *C25B 11/00* | (2006.01) |
| *C25B 13/00* | (2006.01) |
| *G01N 31/00* | (2006.01) |
| *G01N 33/50* | (2006.01) |
| *G01N 17/00* | (2006.01) |
| *G01N 27/26* | (2006.01) |
| *A61B 5/00* | (2006.01) |
| *G01F 1/64* | (2006.01) |

(52) U.S. Cl. ............... 204/403.13; 205/792; 977/924

(58) Field of Classification Search ............ 205/792, 205/794.5; 204/786, 403.13, 290.14; 429/401
See application file for complete search history.

(56) References Cited

U.S. PATENT DOCUMENTS

| | | | |
|---|---|---|---|
| 5,312,527 A | 5/1994 | Mikkelsen et al. | |
| 6,660,480 B2 | 12/2003 | Ramsey et al. | |
| 6,713,519 B2 * | 3/2004 | Wang et al. ............ | 518/715 |
| 6,958,216 B2 | 10/2005 | Kelley et al. | |
| 7,202,037 B2 | 4/2007 | Barton et al. | |
| 7,258,838 B2 | 8/2007 | Li et al. | |
| 7,279,337 B2 | 10/2007 | Zhu | |
| 2005/0058990 A1 | 3/2005 | Guia et al. | |
| 2005/0276743 A1 * | 12/2005 | Lacombe et al. ........ | 423/447.3 |
| 2006/0246438 A1 | 11/2006 | McCall et al. | |

(Continued)

FOREIGN PATENT DOCUMENTS

WO 2006110347 A2 10/2006

OTHER PUBLICATIONS

Drummond,T. G., Hill, M. G., Barton, J. K. "Electrochemical DNA Sensors." Nature Biotechnology, vol. 21, No. 10, Oct. 2003, pp. 1194-1199.*

(Continued)

*Primary Examiner* — Jeffrey T Barton
*Assistant Examiner* — Louis Rufo
(74) *Attorney, Agent, or Firm* — Polsinelli Shughart PC

(57) ABSTRACT

A sensor electrode for the detection of nucleotides in a biological sample is described. The sensitivity of the electrode is enhanced by the nanostructured sensor architecture that increases the available surface area of the electrode. The electrode detects nucleotides using standard electrochemical methods.

27 Claims, 6 Drawing Sheets

U.S. PATENT DOCUMENTS

2007/0178477 A1* 8/2007 Joiner et al. ............ 435/6
2007/0256562 A1* 11/2007 Routkevitch et al. ............ 96/11
2010/0288651 A1* 11/2010 Compton et al. ............ 205/780.5

OTHER PUBLICATIONS

Bae et al., "Selective Growth of Carbon Nanotubes on Pre-patterned Porous Anodic Aluminum Oxide", Advanced Materials, 2002, pp. 277-279, vol. 14, No. 4.

Koehne et al., "The fabrication and electrochemical characterization of carbon nanotube nanoelectrode arrays", Journal of Materials Chemistry, 2004, pp. 676-684, vol. 14, No. 4.

Wang et al., "DNA biosensors based on self-assembled carbon nanotubes", Biochemical and Biophysical Research Communications, 2004, pp. 1433-1437, vol. 325, No. 4.

Written Opinion and International Search Report for PCT/US09/36547 dated Mar. 3, 2010, 11 pages.

Drummond et al., "Electrochemical DNA sensors", Nature Biotechnology, 2003, pp. 1192-1199, vol. 21, No. 10.

Erdem et al., "Direct DNA Hybridization at Disposable Graphite Electrodes Modified with Carbon Nanotubes", Analytical Chemistry, 2006, pp. 6656-6659, vol. 78, No. 18.

Gasparac et al., "Ultrasensitive Electrocatalytic DNA Detection at Two- and Three-Dimensional Nanoelectrodes", Journal of American Chemical Society, 2004, pp. 12270-12271, vol. 126.

Gu et al., "DNA Sensor for Recognition of Native Yeast DNA Sequence with Methylene Blue as an Electrochemical Hybridization Indicator", Electroanalysis, 2002, pp. 949-954, vol. 14, No. 13.

He at al., "Aligned carbon nanotube-DNA electrochemical sensors", Chemical Communtions, 2004, pp. 348-349, vol. 3.

Kelley et al., "Long-Range Electron Transfer through DNA Films", Angewandte Chemie International Edition, 1999, pp. 941-945, vol. 38, No. 7.

Lapierre-Devlin et al., "Amplified Electrocatalysis at DNA-Modified Nanowires", Nano Letters, 2005, pp. 1051-1055, vol. 5, No. 6.

Liao et al., "Use of Electrochemical DNA Biosensors for Rapid Molecular Identification of Uropathogens in Clinical Urine Specimens", Journal of Clinical Microbiology, 2006, pp. 561-570, vol. 44, No. 2.

Mascini, "Affinity electrochemical biosensors for pollution control", Pure and Applied Chemistry, 2001, pp. 23-30, vol. 73, No. 1.

Steel et al., "Electrochemical Quantitation of DNA Immobilized on Gold", Analytical Chemistry, 1998, pp. 4670-4677, vol. 70.

* cited by examiner

SENSOR ELECTRODE AND METHOD FOR THE ELECTROCHEMICAL DETECTION OF NUCLEOTIDES

FIELD OF THE INVENTION

The present invention relates generally to nucleotide detection devices, and in particular to an electrochemical nucleotide sensor electrode with a nanoarchitectural design.

BACKGROUND

In a growing number of fields such as clinical medicine, medical and biological research, homeland security, food safety, and water quality, there is an increasing need for the rapid detection of organisms. In particular, there is a critical need for rapid, field-deployable, and highly sensitive methods, which are more dependable and robust than the commonly used polymerase chain reaction (PCR). Specific nucleotides provide evidence of the presence of microbes (such as bacteria, viruses, and protozoa) in the environment.

To address the need for faster, more sensitive and more accurate detection of biological molecules, nucleotide biosensors have been developed. The majority of biosensors commonly used are optical sensors that measure the fluorescence of molecular markers. The markers quantify the presence of particular nucleotides. These fluorescence-based optical biosensors are highly sensitive, but require complicated reagents and markers, expensive instrumentation, and sophisticated numerical algorithms to interpret the data. These requirements typically limit these methods to use in research laboratories.

Electrochemical nucleotide biosensors have been developed that use measurements connected with the oxidation or reduction of nucleotides. Sensors that utilize direct oxidation of the nucleotide exhibit good sensitivity, but this technique requires the use of high electric potentials, which introduces significant background signals that must be filtered. Other sensors utilize the indirect oxidation of nucleotides using a redox moiety that is bound to certain locations in the nucleotide sequence, such as the guanine bases. However, indirect oxidation sensors have several disadvantages including the difficulty of preparing the probe's substrate, the destruction of the sample during the sensing process, and the dependence on complex sensor instrumentation to ensure high sensitivity.

Other sensor designs use cyclic voltammetric methods coupled with indirect nucleotide oxidation to detect the presence of a target nucleotide. Using cyclic voltammetry methods, these sensors measure the flow of electrons through the sensor electrode in response to an applied time-varying electric potential. The sensors that utilize this design are sensitive, and require less complex instrumentation. However, the substrates typically used to fabricate these sensors are difficult to prepare, due to the complexity of the probe nucleotide molecules used in the sensors. In one design, the probe molecule is a nucleotide attached to a compound that must change conformation after the nucleotide is hybridized in order to generate a signal. In a second design, a signal is generated by the hybridization of the probe nucleotide by both the target nucleotide, and an additional signal nucleotide.

Several other sensor designs increase the probe's available surface area by incorporating nanostructures into the sensor architecture. In this type of sensor design, nanostructures such as carbon nanotubes (CNTs) are affixed to each of two electrical terminals of the sensor in precise alignment, resulting in an electrical connection between the two terminals. Although these designs are more sensitive than previous designs due to their increased surface area, the fabrication of these sensors requires a difficult and expensive process of tightly controlled deposition of CNTs in order to assure that appropriate electrical connections are achieved.

There is a need in the art for a nucleotide detection device that is sensitive, simple to fabricate, does not require complicated measuring equipment, and that can be used outside of the laboratory environment. A need exists for a nucleotide detection device that combines the advantages of cyclic voltammetric measurement techniques, indirect nucleotide oxidation methods, and nanostructures, yet minimizes the disadvantages previously associated with these features. To enhance affordability, the sensor should conduct measurements using relatively inexpensive supplies and equipment, and should be reusable.

SUMMARY

The present invention describes devices for measuring the presence and quantity of target nucleotides in a biological sample. An exemplary device includes a nucleotide sensor electrode that combines a novel nanoarchitectural sensor design with proven electrochemical detection methods. The nanoarchitectural design of the nucleotide sensor electrode incorporates nanostructures that allow for greater available surface area for the electrodes and reduced diffusion resistance of the target nucleotides. The fabrication of the nucleotide sensor electrode includes direct growing of multi-walled carbon nanotubes (MWCNTs) onto a substrate perforated with numerous pores and channels. The pores and channels have internal diameters of 10 mm or less. The incorporation of these nanostructures into the nucleotide sensor electrodes results in enhanced detection sensitivity and hybridization efficiency. As such, a substrate is utilized which has a plurality of pores, with MWCNTs located within the pores. Nucleotide probes are affixed to the surface of the substrate and MWCNTs. The electrode will have a surface area of between 7 $cm^2$ and 12 $cm^2$, more preferably 9 $cm^2$.

The nucleotide sensor electrode of the present invention includes a substrate with micro-/nano-fluidic channels. The substrate is typically a nanoporous anodic alumina oxide (AAO) membrane with a plurality of multi-walled carbon nanotubes (MWCNTS) affixed to the surface of the substrate, including the interior of the fluidic channels of the substrate. In addition, a plurality of probe nucleotides is affixed to the surface of the MWCNTs as well as the interior walls of the channels in the substrate. As such, the device includes a substrate, with MWCNTs located on the surface. Affixed to the MWCNTs are nucleotides which, when hybridized, generate a detectable signal. The signal is received and measured to indicate the presence and quantity of a target nucleotide. The cyclic voltammetric methods used by the nucleotide sensor electrode require relatively inexpensive equipment and existing data analysis techniques. The method of direct detection of electronic signals resulting from the hybridization of target nucleotides in the biological sample to the probe nucleotides of the nucleotide detection electrode is robust, rapid, and ideal for field use. Further, the nucleotide sensor electrode may be cleaned and reused.

To detect nucleotides, the sensor electrode is placed in contact with an aqueous solution, such as a water sample, containing target nucleotide molecules. When the probe nucleotides encounter complimentary target nucleotides, hybridization occurs. The hybridized probe nucleotides are electrically conductive compared to the unhybridized probe nucleotides. Changes in the electrical properties of the nucleotide sensor are measured to determine the presence and quantity of target nucleotides. This is done using existing electrochemical measurement techniques, such as cyclic voltammetry and chronocoulometry. Also, a second electron acceptor can be added to the electrolyte solution.

DETAILED DESCRIPTION OF THE INVENTION

The present invention describes a nucleotide sensor electrode 10 with a nanoarchitectural design used for measuring the presence and quantity of target nucleotides 20. The sensor electrode 10 is designed to use an electrochemical method to analyze the target nucleotides 20. Importantly, the electrode 10 has a fluidic channel structure and comparatively high surface area. The sensor electrode 10 utilizes nanostructures in the form of the substrate 30 and multi-walled carbon nanotubes 32. The combination of these two structures results in enhanced detection sensitivity compared to existing nucleotide sensor designs. The sensor electrode may be used to detect nucleotides in a variety of applications, including clinical medicine, medical and biological research, homeland security, food safety, water quality and environmental monitoring.

Figure 1:
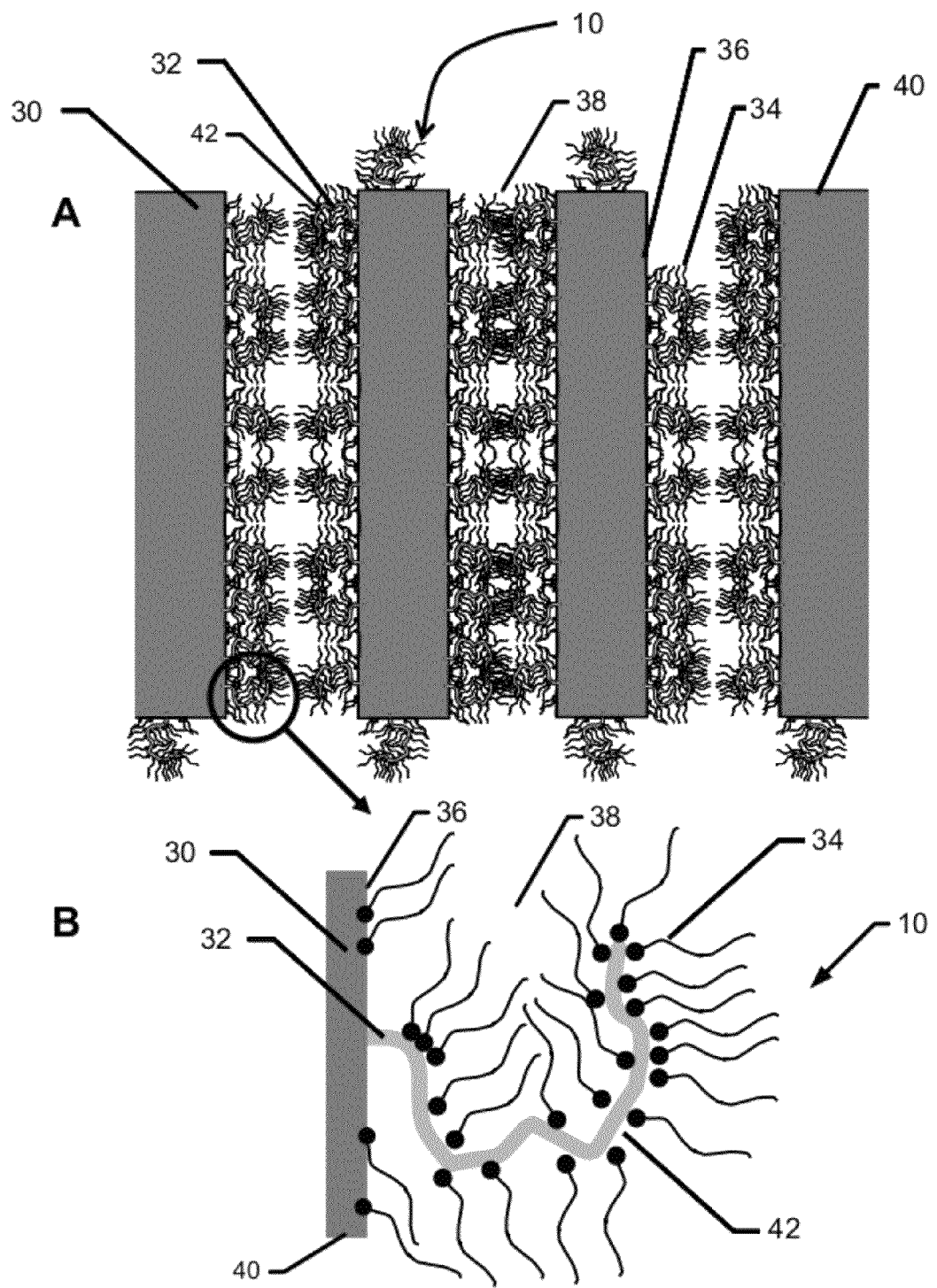
FIG. 1 is a side section (FIG. 1A) and a top view (FIG. 1B) of the nucleotide sensor electrode.

FIG. 1 is an overview of the components of the nucleotide sensor electrode 10. In particular, FIG. 1A is a side cutaway view showing the construction. FIG. 1B is a close-up of the side cutaway view, showing a multi-walled carbon nanotube (MWCNT) 32. The sensor electrode 10 includes a substrate 30, and a plurality of multi-walled carbon nanotubes (MWCNTs) 32 affixed to the interior walls 36 and external surface 40 of the substrate 30. A plurality of probe nucleotides 34 are affixed to the surface 42 of the MWCNTs 32 and to the interior walls 36 of the substrate 30. The interior walls 36 define the interior surface of micro-/nano-channels 38 that may carry fluid though the substrate 30.

A variety of target nucleotide sequences 20 may be detected upon hybridization with the probe nucleotides 34. The target nucleotides 20 are any composition containing nucleotides sufficiently distinct to detect the presence of target nucleotides 20. Included are bacteria, viruses, protozoa, invertebrate animals, vertebrate animals, recombinant nucleotide sequences, and other genetically engineered nucleotide sequences.

DNA and RNA may be extracted from the cells of organisms using known techniques or commercially available kits. The nucleotide strands may be separated using heat or denaturing reagents, or other available methods. Once the target nucleotides 20 are separated into single strands, they are ready to be hybridized with the immobilized single strand nucleotide probes 34.

The substrate 30 may be fabricated from a variety of materials provided that the finished substrate 30 possesses a large surface area per unit volume. Exemplary materials that can be used are microporous anodic alumina oxide (AAO), nanoporous AAO, and combinations thereof. Porous AAO material is commercially available as a membrane filter material, or porous AAO film membranes may be grown using known techniques. In addition, any ceramic or metallic membranes may be used, including ceramic membrane filter elements, sintered metal membranes, frit membranes, metallic membranes, and asymmetric metallic membranes. The thickness of the substrate 30 ranges between about 0.5 mm and about 100 mm, and more preferably between about 40 mm and about 80 mm, and most preferably about 60 mm. The average pore diameter ranges between about 10 nm and about 10,000 nm, more preferably between about 10 nm and about 1000 nm, and most preferably between about 50 nm and about 1000 nm. The average total pore volume ranges between about 20% and about 90% of the total substrate 30 volume. The average pore density ranges between about $10^9$ pores/$cm^2$ and about $10^{11}$ pores/$cm^2$.

The multi-walled carbon nanotubes (MWCNTs) 32 are multiple layers of graphite that form a tubular shape with an outer diameter ranging between about 5 nm and about 70 nm, and a length ranging between about 5 nm and about 4000 nm. The lengths resulting from the process of forming the MWCNTs 32 are selected to fit within the interior walls 36 of the substrate 30. The thin and elongated MWCNTs 32 project away from the exterior surface 40 and interior walls 36 of the substrate 30 and increase the overall surface area of the nucleotide sensor electrode 10. The MWCNTs 32 are affixed to the substrate 30 via deposition. The MWCNTs 32 are deposited on the substrate 30 using known methods such as laser ablation, chemical vapor deposition (CVD), and plasma enhanced chemical vapor deposition (PECVD). A preferred method of depositing the MWCNTs 32 is CVD using a graphite feedstock with imbedded nickel catalyst particles. The amount of MWCNTs 32 deposited is dependent on the starting material and conditions of deposition.

The probe nucleotides 34 are complimentary to the target nucleotide 20. In particular, the probe nucleotides 34 are designed to specifically hybridize with a desired target nucleotide sequence 20. The probe nucleotide 34 may be of a variety of lengths, and includes any nucleotide sequence of less than about 100 nucleotides. The probe nucleotide 34 may be a commercially available nucleotide designed to bind a specific sequence. Conversely, the probe nucleotide 34 may be obtained using known techniques such as nucleotide extraction, replication, amplification, synthesis and combinations thereof. Such a step is taken to form a probe nucleotide 34 complimentary to a particular target nucleotide 20.

The sensor electrode 10 may also include a metal coating 44 to provide an electrically conductive surface to which the probe nucleotides 34 are affixed. The metal coating 44 lowers the overall resistance of the nucleotide sensor electrode 10. Any non-reactive and electrically conductive noble metal may be used for the metal coating 44, including gold, silver, tantalum, platinum, palladium, rhodium, and combinations thereof. The metal coating 44 has a thickness ranging between about 2 nm and about 10 nm, and preferably a thickness ranging between about 2 nm and about 5 nm. The metal coating 44 is affixed to the substrate 30 and MWCNTs 32 using known processes such as sputter coating, electrophoretic deposition, or electroless deposition. The preferred metal coating 44 is a layer of gold that is electroless deposited to a thickness of about 5 nm. Once the surfaces are coated, the probe nucleotides 34 may be affixed to the metal coating 44.

Figure 2:
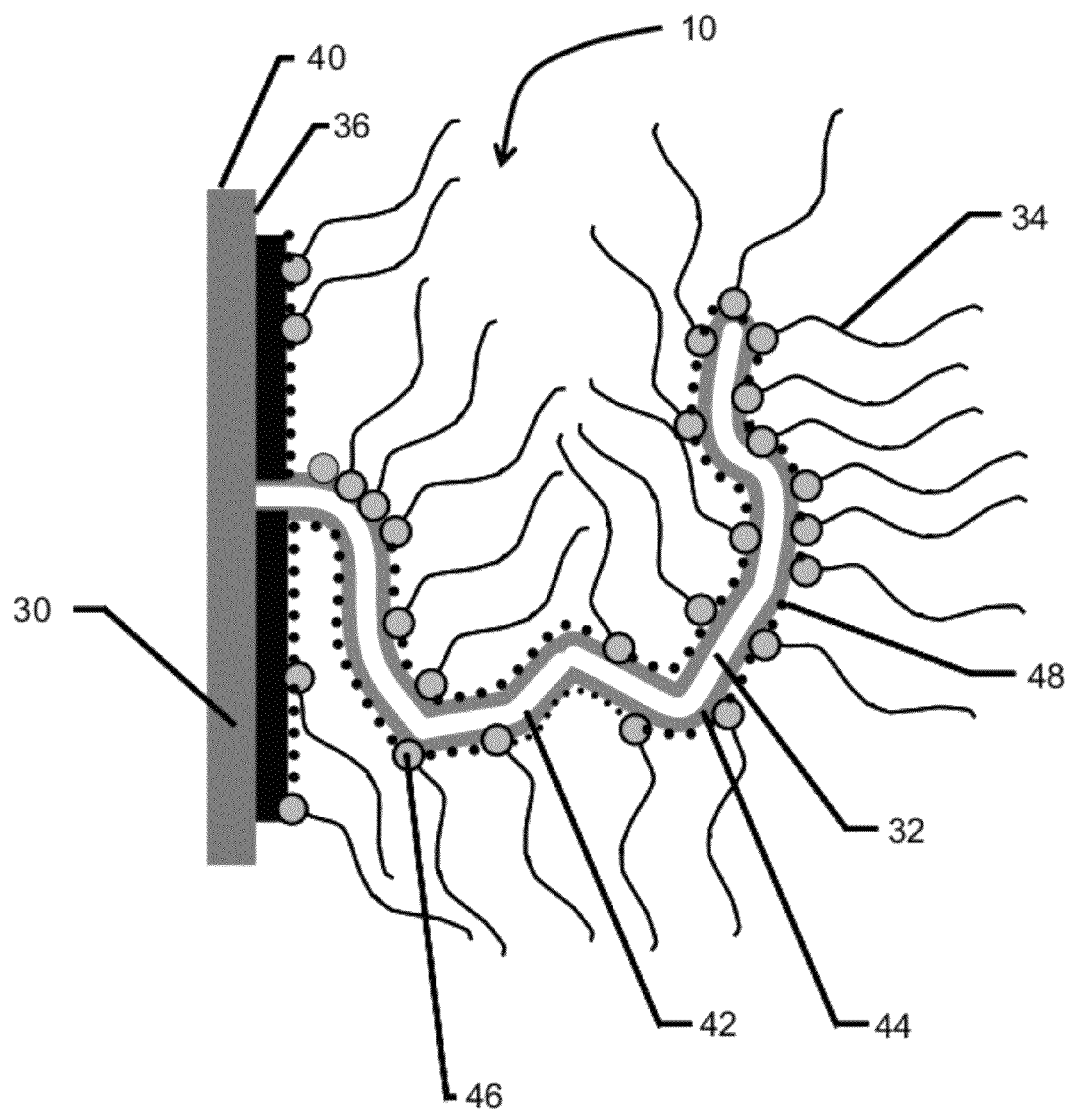
FIG. 2 is a close-up side section of one embodiment of the nucleotide sensor electrode.

The probe nucleotides 34 are affixed to the metal coating 44 using a coupling agent 46, as shown in FIG. 2. The coupling agents 46 are bifunctional linker molecules that possess functional groups that covalently bind to the metal coating 44, and to the probe nucleotides 34. As such, the coupling agents 46 are any of a variety of compounds that link the probe nucleotides 34 to the metal coating 44. One functional group of the coupling agent 46 can contain reactive sulfur atoms that bind covalently with the metal coating 44, including thiol groups, disulfide groups, sulfide groups, and combinations thereof. Another functional group of the coupling agent 46 can be an organic moiety that binds covalently to either terminal of the probe nucleotides 34. Coupling agents 46 include reactive sulfur alkanethiols, linear alkanedithiols, thionucleosides, aromatic ring compounds, sulfolanes, sulfoxides, isonitriles, diimine dithiolate complexes, and combinations thereof. The coupling agent 46 may be bound to the metal coating 44 initially, followed by a reaction to bind the probe nucleotide 34 to the immobilized coupling agent 46. Alternatively, the coupling agent 46 may bind initially to the probe nucleotide 34, and then the functionalized probe nucleotide 34 with attached coupling agent 46 may bind to the metal coating 44.

After affixing the probe nucleotides 34 to the metal coating 44, a non-conductive coating 48 is affixed to any remaining exposed metal coating 44. This coating 48 is affixed to portions of the exposed metal coating 44 using known electrochemical methods. The non-conductive coating 48 prevents the transfer of electrical charge during electrochemical measurements through any path except by way of the hybridized probe nucleotide 34. The inclusion of the non-conductive coating 48 results in enhanced sensitivity of the sensor electrode 10 because of the increased signal-to-noise ratio. The non-conductive coating 48 is an electropolymerization of one or more compounds, including 2-naphthol, diaminobenzene, diaminobenzene copolymerized with dihydroxybenzene, o-aminophenol, p-chlorophenylamine, pyrrole, thiophene, carbozole, and combinations thereof.

To fabricate the sensor electrode 10 shown in FIG. 2, MWCNTs 32 are deposited on the exterior surface 40 and inner walls 36 of the substrate 30. The exterior surface 40 and interior walls 36 of the substrate 30, as well as the surface 42 of the affixed MWCNTs 32, are coated with a metal coating 44. The probe nucleotides 34 are then functionalized with coupling agents 46 and then bonded to the metal coating 44. Alternatively, the coupling agents 46 are bonded to the metal coating 44 and the probe nucleotides 34 are then bonded to the coupling agents 46. In the final step of the fabrication, a non-conductive coating 48 is electropolymerized to any remaining exposed metal coating 44, using known electrochemical techniques. Using this fabrication process, the sensor electrode 10 may be fabricated and stored prior to use.

Figure 3:
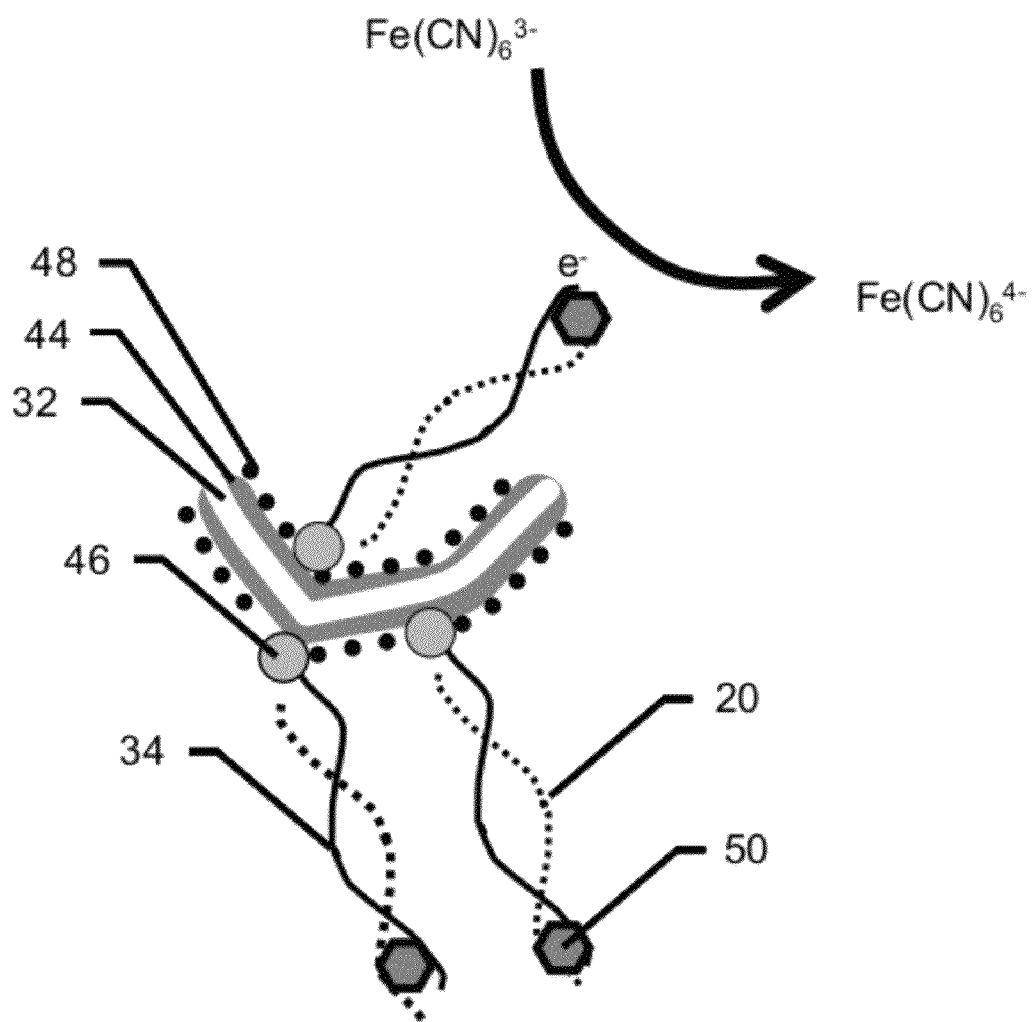
FIG. 3 is a close-up side view of the nucleotide sensor electrode with hybridized target nucleotides.

Target nucleotides 20 are detected using electrochemical measurements conducted using the sensor electrode 10. Initially, the sensor electrode 10 is contacted with an aqueous solution containing the target nucleotides 20. The target nucleotides 20 hybridize with the probe nucleotides 34, as shown in FIG. 3. The hybridized probe nucleotides 34 on the sensor electrode 10, unlike the unhybridized probe nucleotides 34, are capable of conducting electrical charges supplied by the metal coating 44 of the sensor electrode. The sensor electrode 10 is immersed in the solution containing the target nucleotide 20. Alternatively, if the sensor electrode includes a porous membrane substrate 30, the aqueous solution containing the target nucleotides 20 may be induced to flow through the channels of the substrate 30 using known means such as pulling the solution through the channels with vacuum suction or pushing the solution through the channels with pressurized gases.

Once the target nucleotides 20 have hybridized the probe nucleotides 34, the sensor electrode 10 is then contacted with a solution containing electron transfer moieties 50. Upon contact, an electrochemically active nucleotide sensor electrode 10 is formed. The electron transfer moieties 50 are molecules, such as methylene blue, that are capable of intercalating between the double strands of the hybridized probe nucleotides 34. Additionally, the electron transfer moieties 50 can supply charged particles to electrochemical redox reactions. The sensor electrode 10 is then subjected to electrochemical measurements using known equipment and measurement techniques, including cyclic voltammetry and chronocoulometry.

Figure 4:
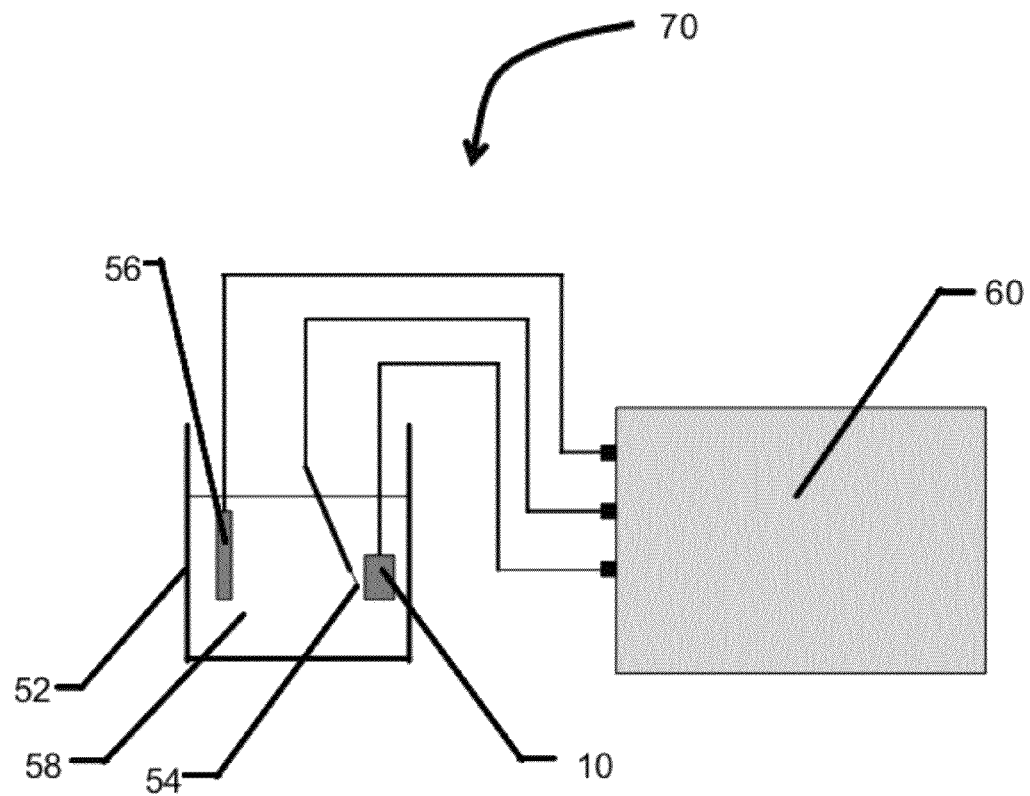
FIG. 4 is a schematic of a typical electrochemical measurement system.

A typical system 70 for conducting electrochemical measurements is illustrated in FIG. 4. The sensor electrode 10 is placed in an electrolyte cell 52, along with a reference electrode 54 and a counter electrode 56. Inside the electrolyte cell, an electrolyte mixture 58 containing ions and redox reactants is added in an amount sufficient to submerge all electrodes. The electrodes are then electrically connected to the electrochemical measurement device 60, such as a potentiostat. Using the electrochemical measurement device 60, the electrical potential supplied to the sensor electrode 10 is varied in a repeating pattern of increasing and decreasing voltage, and the resulting Faradaic current is measured and analyzed. Differences in the electrochemical response of the sensor electrode 10, as measured by the electrochemical measurement device 60, indicate the presence and amount of target nucleotides 20 in the sample.

EXAMPLES

Example 1

A Prototype Nanostructured Nucleotide Detection Electrode was Fabricated

To assess the feasibility of fabricating a nanostructured electrochemical nucleotide detection electrode, the following experiment was conducted. An inorganic filtration membrane (Anodisc 25, Whatman International Ltd., England) composed of anodic aluminum oxide, was used as the substrate for the electrode. The membrane had a thickness of 60 µm, a diameter of 21 mm, an average pore size of 200 nm, and a porosity of 25~50%. A polypropylene ring around the outer circumference of the membrane supported the membrane.

The membrane substrate was coated with gold to a thickness of less than 10 nm. Electroless gold plating was used to deposit gold coatings on the membrane substrate surfaces as well as on the channel walls inside the pores. The membrane substrate was immersed into methanol for 5 minutes prior to immersion in a solution of 0.025 M of $SnCl_2$ and 0.07 M of trifluoroacetic acid for 45 minutes. This yielded Sn-sensitized membrane substrates, which were then immersed in 0.029 M aqueous $AgNO_3$ solution for 10 minutes. After washing in methanol for five minutes, these AAO templates were immersed into a gold-plating bath, containing 0.5 mL of the commercial gold plating solution, which contains 0.127M of $Na_2SO_3$, 0.625M of formaldehyde, and 0.025 M of $NaHCO_3$. By adding $H_2SO_4$ with continuous stirring, the pH value of plating solution was adjusted to 9~10. Energy dispersive spectra (EDS), obtained using Noran Vantage EDS with Hitachi S4700 Scanning Electron Microscope (SEM), confirmed that gold coating had deposited on the AAO substrate top surface and inner walls of the channels.

Probe nucleotide attachment was first performed by a self-assembled monolayer (SAM) of 3-mercaptopropionic acids into the Au-AAO surface, which acted as bridges between the gold coating and probe nucleotides. Ethanol solution containing 1% 3-mercaptopropionic acid by volume was prepared. The gold-coated AAO substrate was submerged in the solution for 24 hours. Although the chemical adsorption of thiol groups into the gold coating finishes in a short period of time and the bonding energy is also high, a highly ordered monolayer was obtained after 24 hours of submersion. The substrate was then submerged into the solution containing 2 mM of probe nucleotides in 5 mM phosphate and 50 mM of NaCl (pH 7.0). Probe DNA electrodes thus prepared were thoroughly washed with distilled water and stored at 4° C.

The results of this experiment demonstrated the successful fabrication of a nanostructured nucleotide detection electrode that could be used to electrochemically detect target nucleotides in aqueous solution.

Example 2

A Prototype Nanostructured Nucleotide Detection Electrode Incorporating Multi-Walled Carbon Nanotubes was Fabricated To assess the feasibility of growing carbon nanotubes on a nanostructured substrate, the following experiment was conducted. An inorganic filtration membrane, described in Example 1, was used as a substrate on which to grow multi-walled carbon nanotubes (MWCNTs). MWCNTs were grown on the membrane substrate using a chemical vapor deposition (CVD) process. The membrane was placed in a thermal CVD system at a temperature ranging between 600° C. and 1000° C. and a pressure of about 10 torr. In the thermal CVD system, laser pulses were used to vaporize a graphite feedstock with imbedded nickel catalyst particles, and the vaporized carbon atoms accrued on the membrane substrate as MWCNTs. MWCNTs were grown on the membrane substrate for approximately three hours, and the resulting membrane with MWCNTs was then electrochemically coated with gold particles to a maximum thickness of 10 nm. This process yielded a membrane with densely packed MWCNTs within the nanopores of the membrane, as measured by scanning electron microscope.

The results of this experiment demonstrated that MWCNTs may be directly grown within the nanopores of a membrane, vastly increasing the surface area on which to bind the nucleotide probes used in the nucleotide detection electrode.

Example 3

A Prototype Electrochemical Nucleotide Detection Device was Used to Detect *Bacteroides thetaiotaomicron* in a Water Sample To determine the effectiveness of using a nanotechnology-based electrochemical nucleotide sensing apparatus to measure the presence of a nucleotide, the following experiment was conducted. Nucleotides from *Bacteroides thetaiotaomicron*, a bacteria present in the human intestine and reported as an indicator of water quality, were measured using a conventional nucleotide sensing electrode and compared to similar measurements taken using a nanostructured nucleotide sensing electrode.

The conventional nucleotide detection electrode was an electrode made of gold metal only. The nanostructured nucleotide detection electrode was constructed by layering gold over the surface of nanoporous anodic alumina oxide (AAO), as described in Example 1. The surface area of the conventional electrode was 0.07065 $cm^2$, and the surface area of the nanoporous AAO electrode was 9.04 $cm^2$, nearly 130 times more than the conventional electrode.

The 19 base pair nucleotide probes used for the sensor electrodes were synthesized and the following primer sequences (Integrated DNA Technologies, USA), derived from the bacterial organism, *Bacteroides thetaiotaomicron*, a marker for human fecal contamination in water:

```
Probe:    5'ATC GGC AGA CTG CGA CTT T3'

Target:   3'TAG CCG TCT GAC GCT GAA A'5'
```

The nucleotide probes were immobilized to the gold layer of the sensor electrodes using thiol coupling agents.

After the nucleotide probes were immobilized, any remaining exposed gold layer was coated with a poly-2-naphthol film that was electrochemically polymerized. Each sensor electrode with immobilized probe nucleotides was immersed in an electrolyte cell containing 1.4417 g of 2-naphthol dissolved in 100 ml of a solution containing 50% acetonitrile and 50% buffer solution (5 mM phosphate and 50 mM NaCl at a pH of 7.0). Electric potentials to the sensor electrode were then varied from 0 to 700 mV for several minutes at a scan rate of 50 mV/s until the cycling electrode potential induced no measurable electrical current.

The sensor electrodes were hybridized by immersing the electrodes into the aqueous solution containing the target single-stranded DNA for 60 minutes at room temperature.

After the hybridization of the nucleotide detection electrode, the electrode was placed in an electrolyte cell containing 50 mM Tris-HCl, 20 mM NaCl, and 50 mM $K_3Fe(CN)_6$. 1% aqueous methylene blue (MB) solution was also added to the electrolyte solution to load the hybridized nucleotides of the sensor electrode with an intercalator to enhance the conductivity of the hybridized probe nucleotides. In addition, the electrolyte cell also contained a counter electrode and reference electrode. All electrodes were connected to a potentiostat (Model 273A, EG&G Princeton Applied Research, USA), and electrochemical measurements were acquired by a multiplexer (Model 314, EG&G Princeton Applied Research, USA). The measurements thus acquired were analyzed using Power Suite software (EG&G Princeton Applied Research, USA).

The electrochemical measurement techniques included cyclic voltammetry (CV) and chronocoulometry (CC). During the electrochemical measurements, the DNA detection electrodes were used as working electrodes along with the platinum counter electrode, and a standard Ag/ACL (saturated KCl) electrode was used as the reference electrode. When the target nucleotides hybridized to the probe, a perfectly matched double-stranded DNA molecule was formed that readily conducted electrons from the gold layer of the DNA detection probe to the electrolyte solution. The electrons in solution initiated reduction reactions with the $(Fe(CN)_6)^{3-}$ ions in the electrolyte solution, reducing them to $(Fe(CN)_6)^{4-}$ ions. The reduction reaction generated a minute electric current that was rapidly detected by the potentiostat. Measurements took place over a period ranging between 30 seconds and five minutes.

Figure 5:
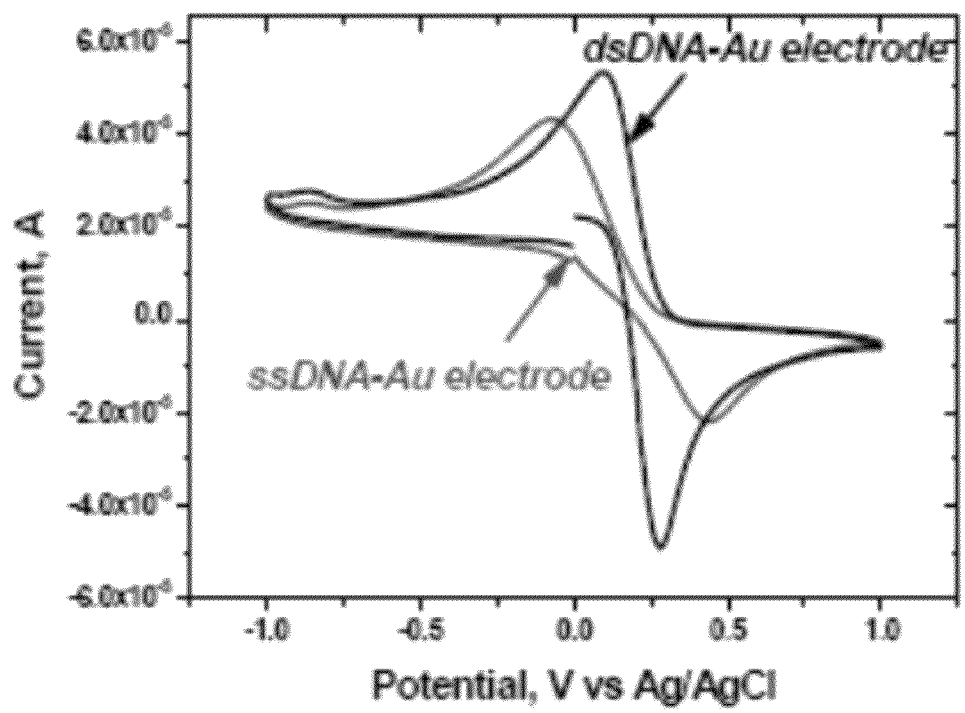
FIG. 5 is a comparison of the cyclic voltammetric response measured using a conventional gold DNA sensing electrode with, and without, hybridization of the probe DNA, as described in Example 3.

The results of the CV analysis using measurements from the conventional DNA sensing electrode are shown graphed in FIG. 5. The current responses of the conventional DNA sensing probe without hybridization (ssDNA-Au electrode) and with hybridization (dsDNA-Au electrode) are compared. Due to the increased conductivity of the dsDNA, the dsDNA-Au probe is more responsive to the variations in electrode potential, as evidenced by the larger differences in minimum and maximum current measured during a potential cycle.

Figure 6:
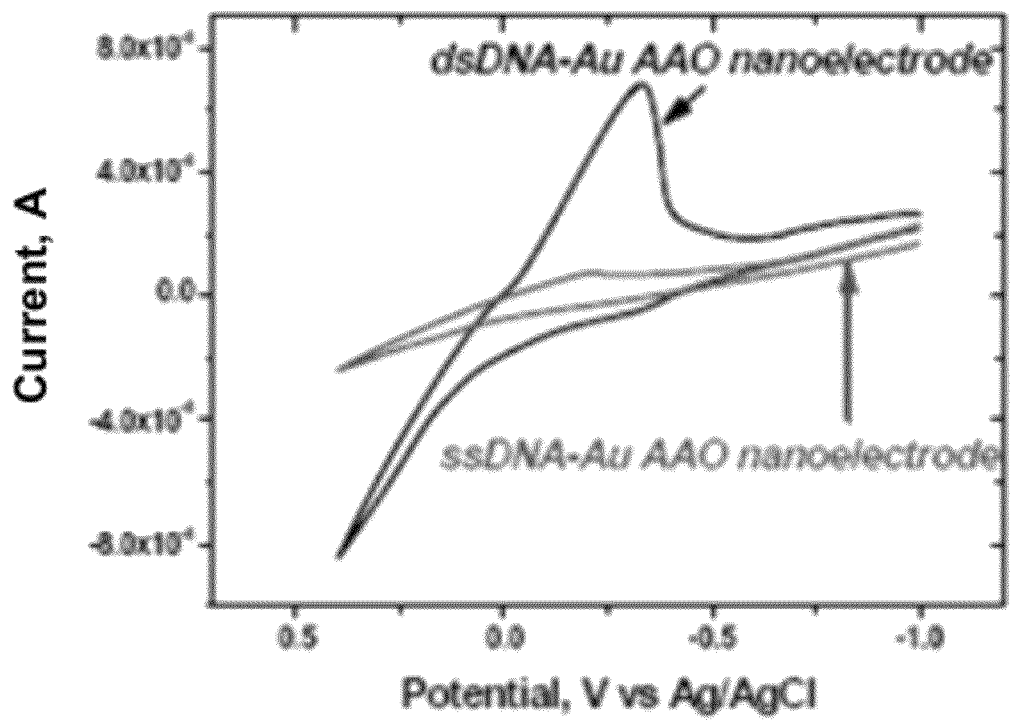
FIG. 6 is a comparison of the cyclic voltammetric response measured using a nanostructured DNA sensing electrode with and without hybridization of the probe DNA, as described in Example 3.

FIG. 6 is a similar comparison to that made in FIG. 5 for the nanostructured DNA sensing electrode (AAO nanoelectrode). The hybridized electrode (dsDNA-Au AAO electrode) was more responsive relative to the non-hybridized electrode (ssDNA-Au AAO electrode). Comparing the results for the conventional DNA sensing electrode as shown in FIG. 5 to the results for the nanostructured DNA sensing electrode as shown in FIG. 6, the responsiveness of the nanostructured DNA sensing electrode was enhanced.

Table 1 is a summary of the results for both the chronocoulometry (CC) measurements as well as the CV results. In this table, $\Delta Q$, the increase in charges that flow during a potential cycle due to the hybridization of the ssDNA probes, was over 9-fold higher for the nanostructured DNA detection probe relative to the conventional DNA detection probe. Further, $\Delta i_{pc}$, the difference in current response during a potential cycle for the hybridized DNA detection probes, was over 10-fold greater for the nanostructured DNA detection electrode relative to the conventional DNA detection electrode.

TABLE 1

Electrochemical measurement results for the conventional and nanostructured DNA detection electrodes.

| Electrode Type | $\Delta Q$ | Surface Area of Electrode (cm$^2$) | $\Delta i_{pc}$ of dsDNA electrode (A) |
|---|---|---|---|
| Conventional Au electrode | 31.1% | 0.07065 | $5.33 \times 10^{-5}$ |
| Au-AAO nanoelectrode | 275.6% | 9.04 | $6.83 \times 10^{-4}$ |

The results of this experiment demonstrated the feasibility of using the detection of current generated by MB-intercalated hybridized DNA probes to detect the presence of DNA. Further, the use of nanostructured DNA detection electrodes increased the sensitivity of this technique for the detection of DNA.

Example 4

The Effect of Electrocatalysis on the Detection Sensitivity of a Prototype Electrochemical Nucleotide Detection Device was Assessed To determine the effect of including different combinations of ions in the electrolyte solution on the sensitivity of measurements conducted with a prototype electrochemical nucleotide sensing apparatus, the following experiment was conducted.

Nucleotides from *Bacteroides thetaiotaomicron* were measured using a conventional nucleotide sensing electrode and a nanostructured nucleotide sensing electrode using the sensing electrodes and methods described in Example 3.

An electrochemical characterization system (Potentiostat/Galvanostat Model 273A with Power Suite, EG&G Princeton Applied Research) was used to measure the cyclic voltammograms of the DNA electrodes in an electrolyte solution of 50 mM Tris/20 mM NaCl (pH 7.2) and redox pairs with a three-electrode setup using Ag/AgCl (saturated KCl) as the reference electrode. The redox pairs used for electrochemical measurements were potassium ferricyanide ($K_4[Fe(CN)_6]$) and hexaaminorutheniumchloride ($[Ru(NH_3)_6]Cl_3$) alone and in combination.

To quantify the DNA hybridization, cathodic charge (Q) was obtained by integrating the area under each CV curve. The signal changes ($\Delta Q$ values) corresponding to hybridization were calculated and are summarized in Table 2. The average $\Delta Q$ values of 28.2~31.1% for the bulk gold DNA macroelectrode, and 235.1~482.9% for the nanostructured DNA probe electrodes indicated a 10-fold increase in hybridization efficacy due to the use of nanostructures in the electrode.

The electrochemical response of the synthesized nanostructured DNA probe electrodes by CV measurements was also measured using an electrocatalytic reporter system with $Ru(NH_3)_6^{3+}$ as a primary acceptor and $Fe(CN)_6^{3-}$ as a secondary acceptor. Electrocatalysis at the prototype nanostructured DNA probe electrodes amplified the detection signal and essentially doubled the value achieved using one type redox pairs of $Fe(CN)_6^{3-}$ in the electrolyte.

TABLE 2

Electrochemical measurement results for the conventional and nanostructured DNA detection electrodes with different electrolyte solutions.

| DNA probe electrodes | Redox pairs in electrolyte solutions | $\Delta i_{pc}$ (µA) | $\Delta Q$ (%) |
|---|---|---|---|
| Conventional Au electrode | 50 µM Fe(CN)$_6$ | 9.52 | 31.1 ± 14.5 |
|  | 20 µM Ru(NH$_3$)$_6$ | 21.83 | 28.2 ± 12.5 |
| Au-AAO nanoelectrode | 50 µM Fe(CN)$_6$ | 683.2 | 275.6 ± 65.0 |
|  | 20 µM Ru(NH$_3$)$_6$ | 508.2 | 235.1 ± 40.0 |
| Au-AAO nanoelectrode + Electrocatalysis | 40 µM Fe(CN)$_6$ + 10 µM Ru(NH$_3$)$_6$ | 805.6 | 412.7 ± 45.0 |
|  | 10 µM Fe(CN)$_6$ + 40 µM Ru(NH$_3$)$_6$ | 1063.9 | 482.9 ± 40.0 |

The results of this experiment demonstrated that the sensitivity of the prototype nanostructured electrochemical DNA probe was essentially doubled through the introduction of a second redox ion into the electrolyte solution.

While the invention has been explained in relation to exemplary embodiments, it is to be understood that various modifications thereof will become apparent to those skilled in the art upon reading the description. Therefore, it is to be understood that the invention disclosed herein is intended to cover such modifications as fall within the scope of the appended claims.

What is claimed is:

1. A nucleotide sensor electrode with a nanoarchitectural design, comprising:
    a. a substrate comprising a pair of opposed external surfaces separated at a substrate thickness, wherein the substrate further forms a plurality of inner walls extending through the substrate thickness, defining a plurality of micro-/nano-fluidic channels;
    b. a plurality of MWCNTs, each MWCNT comprising a tubular shape affixed at one end to either one of the external surfaces or one of the inner walls, wherein a first portion of the plurality of MWCNTs project from the external surfaces, and a second portion of the plurality of MWCNTs project from the inner walls;
    c. a metal coating affixed to the pair of external surfaces, the plurality of inner walls, and the plurality of MWCNTs; and d. a plurality of probe nucleotides affixed to the metal coating.

2. The electrode of claim 1, wherein the substrate is selected from the group consisting of microporous anodic alumina oxide, nanoporous anodic alumina oxide, and combinations thereof.

3. The electrode of claim 1, wherein the substrate is selected from the group consisting of ceramic membranes, and metallic membranes.

4. The electrode of claim 1, wherein the thickness of the substrate ranges between about 0.5 µm and about 100 µm.

5. The electrode of claim 1, wherein the thickness of the substrate ranges between about 40 µm and about 80 µm.

6. The electrode of claim 1, wherein the thickness of the substrate is about 60 µm.

7. The electrode of claim 1, wherein the average channel size of the substrate ranges between about 10 nm and about 10,000 nm.

8. The electrode of claim 1, wherein the average channel size of the substrate ranges between about 10 nm and about 1,000 nm.

9. The electrode of claim 1, wherein the average channel size of the substrate ranges between about 20 nm and about 200 nm.

10. The electrode of claim 1, wherein the average pore volume of the substrate ranges between about 20% and about 90% of the total substrate volume.

11. The electrode of claim 1, wherein the average pore density ranges between about $10^9$ pores/cm$^2$ and about $10^{11}$ pores/cm$^2$.

12. The electrode of claim 1, wherein a coupling agent holds the probe nucleotides to the metal coating.

13. The electrode of claim 1, wherein the electrode has a surface area of between 7 cm$^2$ and 12 cm$^2$, wherein the surface area includes the substrate surface, the inner walls, and the MWCNTs.

14. The electrode of claim 13 wherein the electrode has a surface area of 9 cm$^2$.

15. A nucleotide sensor electrode with a nanoarchitectural design, comprising:
   a. a substrate comprising a pair of opposed external surfaces separated at a substrate thickness, wherein the substrate further forms a plurality of inner walls extending through the substrate thickness, defining a plurality of micro-/nano-fluidic channels;
   b. a plurality of MWCNTs, each MWCNT comprising a tubular shape affixed at one end to either one of the external surfaces or one of the inner walls, wherein a first portion of the plurality of MWCNTs project from the external surfaces, and a second portion of the plurality of MWCNTs project from the inner walls;
   c. a metal coating affixed to the pair of external surfaces, the plurality of inner walls, and the plurality of MWCNTs;
   d. a plurality of probe nucleotides affixed to the metal coating; and,
   e. a non-conductive coating affixed to the metal coating between the affixed plurality of probe nucleotides.

16. The electrode of claim 15, wherein the substrate is selected from the group consisting of microporous anodic alumina oxide, nanoporous anodic alumina oxide, and combinations thereof.

17. The electrode of claim 15, wherein the substrate is selected from the group consisting of ceramic membranes, metallic membranes, and combinations thereof.

18. The electrode of claim 15, wherein the thickness of the nanoporous substrate ranges between about 0.5 µm and about 100 µm.

19. The electrode of claim 15, wherein the average pore size of the nanoporous substrate ranges between about 10 nm and about 10,000 nm.

20. The electrode of claim 15, wherein the average pore volume of the nanoporous substrate ranges between about 20% and about 70% of the total substrate volume.

21. The electrode of claim 15, wherein the average pore density ranges between about $10^9$ pores/cm$^2$ and about $10^{11}$ pores/cm$^2$.

22. A nucleotide sensor electrode with a nanoarchitectural design, comprising:
   a. a nanoporous anodic alumina oxide substrate comprising a pair of opposed external surfaces separated at a substrate thickness, wherein the substrate further forms a plurality of inner walls extending through the substrate thickness, defining a plurality of micro-/nano-fluidic channels, and wherein the substrate thickness ranges between about 0.5 µm and about 100 µm, an average channel size ranges between about 20 nm and about 200 nm, a pore volume ranges between about 20% and about 90% of the total substrate volume, and an average pore density ranges between about $10^9$ pores/cm$^2$ and about $10^{11}$ pores/cm$^2$;
   b. a plurality of MWCNTs, each MWCNT comprising a tubular shape affixed at one end to either one of the external surfaces or one of the inner walls, wherein a first portion of the plurality of MWCNTs project from the external surfaces, and a second portion of the plurality of MWCNTs project from the inner walls, and wherein each MWCNT further comprises an outer diameter ranging between about 5 nm and about 70 nm, and a length ranging between about 5 nm and about 4000 nm;
   c. a metal coating, with a thickness ranging between about 2 nm and about 5 nm, affixed to the pair of external surfaces, the plurality of inner walls, and the plurality of MWCNTs;
   d. a plurality of probe nucleotides affixed to the metal coating using a coupling agent; and,
   e. a non-conductive coating affixed to the metal coating between the affixed plurality of probe nucleotides.

23. The electrode of claim 22, wherein the electrode has a surface area of between 7 cm$^2$ and 12 cm$^2$, wherein the surface area includes the substrate surface, the inner walls, and the MWCNTs.

24. A method of detecting target nucleotides using a nucleotide sensor electrode with a nanoarchitectural design, comprising:
   a. contacting the nucleotide sensor electrode of claim 1 with a solution containing a target nucleotide for between about 5 minutes and about 2 hours, resulting in a hybridized sensor electrode;
   b. placing the hybridized sensor electrode in an electrolyte tank containing electrolyte solution, a reference electrode, and a counter electrode;
   c. adding an electron transfer moiety to the electrolyte solution, resulting in an electrically active sensor electrode;
   d. electrically connecting the electrically active sensor electrode, the reference electrode, and the counter electrode in the electrolyte tank to an electrochemical measurement device; and,
   e. conducting electrochemical measurements using the electrically active sensor electrode.

25. A method of detecting target nucleotides using a nucleotide sensor electrode with a nanoarchitectural design, comprising:
   a. contacting the nucleotide sensor electrode of claim 1 with a solution containing a target nucleotide for between about 5 minutes and about 2 hours, resulting in a hybridized sensor electrode;
   b. placing the hybridized sensor electrode in an electrolyte tank containing electrolyte solution, a reference electrode, and a counter electrode;
   c. adding an electron transfer moiety to the electrolyte solution, resulting in an electrically active sensor electrode;
   d. electrically connecting the electrically active sensor electrode, the reference electrode, and the counter electrode in the electrolyte tank to an electrochemical measurement device;
   e. conducting electrochemical measurements using the electrically active sensor electrode; and,
   f. adding a second electron acceptor to the electrolyte solution.

26. A method of using a nucleotide sensor electrode, comprised of a substrate comprising a pair of opposed external surfaces seperated at a substrate thickness, wherein the substrate further forms a plurality of inner walls extending through the substrate thickness, defining a plurality of micro-/nano-fluidic channels, selected from the group consisting of microporous anodic alumina oxide or nanoporous anodic alumina oxide, with a substrate thickness ranging between about 0.5 μm and about 100 μm, an average channel size of the substrate ranging between about 10 nm and about 10,000 nm, an average pore volume of the substrate ranging between about 20% and about 90% of the total substrate volume, and an average pore density of the substrate ranging between about $10^9$ pores/cm$^2$ and about $10^{11}$ pores/cm$^2$; a plurality of MWCNTs, each MWCNT comprising a tubular shape affixed at one end to either one of the external surfaces or one of the inner walls, wherein a first portion of the plurality of MWCNTs project from the external surfaces, and a second portion of the plurality of MWCNTs project from the inner walls; a metal coating affixed to the pair of external surfaces, the plurality of inner walls, and the plurality of MWCNTs; and a plurality of probe nucleotides affixed to the metal by coupling agents, to detect target nucleotides, the method comprising:
   a. contacting the nucleotide sensor electrode with a solution containing a target nucleotide for between about 5 minutes and about 2 hours, resulting in a hybridized sensor electrode;
   b. placing the hybridized sensor electrode in an electrolyte tank containing electrolyte solution, a reference electrode, and a counter electrode;
   c. adding an electron transfer moiety to the electrolyte solution, resulting in an electrically active sensor electrode;
   d. electrically connecting the electrically active sensor electrode, the reference electrode, and the counter electrode in the electrolyte tank to an electrochemical measurement device; and,
   e. conducting electrochemical measurements using the electrically active sensor electrode.

27. A method of using a nucleotide sensor electrode, comprised of a substrate comprising a pair of opposed external surfaces seperated at a substate thickness, wherein the substrate further forms a plurality of inner walls extending through the substrate thickness, defining a plurality of micro-/nano-fluidic channels, selected from the group consisting of microporous anodic alumina oxide or nanoporous anodic alumina oxide, with a substrate thickness ranging between about 0.5 μm and about 100 μm, an average channel size of the substrate ranging between about 10 nm and about 10,000 nm, an average pore volume of the substrate ranging between about 20% and about 90% of the total substrate volume, and an average pore density of the substrate ranging between about $10^9$ pores/cm$^2$ and about $10^{11}$ pores/cm$^2$; a plurality of MWCNTs, each MWCNT comprising a tubular shape affixed at one end to either one of the external surfaces or one of the inner walls, wherein a first portion of the plurality of MWCNTs project from the external surfaces, and a second portion of the plurality of MWCNTs project from the inner walls; a metal coating affixed to the pair of external surfaces, the plurality of inner walls, and the plurality of MWCNTs; and a plurality of probe nucleotides affixed to the metal by coupling agents, to detect target nucleotides, the method comprising:
   a. contacting the nucleotide sensor electrode with a solution containing a target nucleotide for between about 5 minutes and about 2 hours, resulting in a hybridized sensor electrode;
   b. placing the hybridized sensor electrode in an electrolyte tank containing electrolyte solution, a reference electrode, and a counter electrode;
   c. adding an electron transfer moiety to the electrolyte solution, resulting in an electrically active sensor electrode;
   d. electrically connecting the electrically active sensor electrode, the reference electrode, and the counter electrode in the electrolyte tank to an electrochemical measurement device;
   e. conducting electrochemical measurements using the electrically active sensor electrode; and,
   f. adding a second electron acceptor to the electrolyte solution.

* * * * *

UNITED STATES PATENT AND TRADEMARK OFFICE
CERTIFICATE OF CORRECTION

| | | |
|---|---|---|
| PATENT NO. | : 8,202,408 B2 | Page 1 of 1 |
| APPLICATION NO. | : 12/400425 | |
| DATED | : June 19, 2012 | |
| INVENTOR(S) | : Charles A. Carson et al. | |

It is certified that error appears in the above-identified patent and that said Letters Patent is hereby corrected as shown below:

In the Claims:

Col. 14, line 12 (Claim 27, line 3): "seperated at a substate" should read --separated at a substrate--

Signed and Sealed this
Fourth Day of September, 2012

David J. Kappos
*Director of the United States Patent and Trademark Office*